United States Patent [19]

Sabb

[11] Patent Number: 5,510,478
[45] Date of Patent: Apr. 23, 1996

[54] 2-ARYLAMIDOTHIAZOLE DERIVATIVES WITH CNS ACTIVITY

[75] Inventor: Annmarie L. Sabb, Pennington, N.J.

[73] Assignee: American Home Products Corporation, Madison, N.J.

[21] Appl. No.: 347,524

[22] Filed: Nov. 30, 1994

[51] Int. Cl.⁶ .............. C07D 277/46; C07D 417/14; C07D 417/06; C07D 453/02
[52] U.S. Cl. ................. 540/585; 544/295; 544/364; 544/369; 546/112; 546/133; 548/195
[58] Field of Search ............. 548/195; 544/295, 544/369; 546/133; 540/584, 585

[56] References Cited

U.S. PATENT DOCUMENTS

| | | | |
|---|---|---|---|
| 3,872,124 | 3/1975 | Le Martret et al. | 260/268 PH |
| 4,152,329 | 5/1979 | Cahoy | 260/306.8 R |
| 5,324,723 | 6/1994 | Baker et al. | 514/212 |

FOREIGN PATENT DOCUMENTS

| | | |
|---|---|---|
| 0307142 | 3/1989 | European Pat. Off. |
| 0538231 | 4/1993 | European Pat. Off. |

OTHER PUBLICATIONS

K. Fukuda et al., TiPS 4–10 Dec. 1989 Supplement.
T. I. Bonner, TiPS 11–15 Dec. 1989 Supplement.
T. T. Soncrant et al., Psychopharmacology 112:421–427 (1993)**.
M. Williams, Curr. Opin. Invest. Drugs 2(5):541–544 (May 1993).
R. T. Bartus et al., Science 217:408–417 (Jul. 1982).

Primary Examiner—Mukund J. Shah
Assistant Examiner—King L. Wong
Attorney, Agent, or Firm—Richard K. Jackson

[57] ABSTRACT

The compound of the formula:

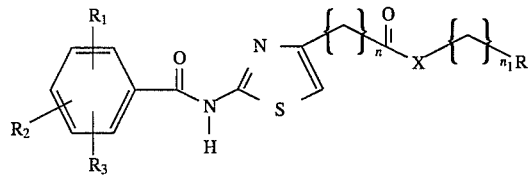

where $R_1$, $R_2$ and $R_3$ are, independently, H, alkyl, halo, perhaloalkyl, hydroxy, alkoxy, aryl or arylalkyl; n is an integer from 0–5; R is azabicyclo[2.2.2]octyl or azabicyclo[2.2.1]heptyl when $n_1$ is zero, or R is $NR_4R_5$ when $n_1$ is 1, 2, 3, 4, or 5, in which $R_4$ and $R_5$ are alkyl or $R_4$ and $R_5$, taken with the nitrogen atom to which they are attached, are N-(substituted aryl)piperazinyl in which said substituent is alkoxy, halo, or perhaloalkyl; N-(pyridyl)piperazinyl; N-(pyrimidinyl)piperazinyl; or 3-azabicyclo-[3.2.2]non-3-yl; X is oxygen or NH; n and $n_1$ are, independently, one of the integers 0, 1, 2, 3, 4 or 5; or a pharmaceutically acceptable salt thereof are centrally active muscarinic agents.

21 Claims, No Drawings

2-ARYLAMIDOTHIAZOLE DERIVATIVES WITH CNS ACTIVITY

BACKGROUND OF THE INVENTION

Cognitive disorders have many components including forgetfulness, confusion, memory loss, attentional deficits, and deficits in visual perception. Some of the symptoms of cognitive disorders are associated with decreased levels of the neurotransmitter, acetylcholine. Neurological illnesses related to cholinergic deficiency include presenile dementia and senile dementia of the Alzheimer's type (SDAT), Parkinson's disease, Downe's Syndrome and dementia pugilistica.

The "cholinergic hypothesis" [R. T. Bartus, et al., Science, 217, 408–417 (Jul. 30, 1982)] suggests that memory loss due to decreased levels of acetylcholine can be ameliorated by correcting the levels of acetylcholine in the brain using an acetylcholine releasing agent, an acetylcholine esterase inhibitor, or by using a drug which mimics acetylcholine (cholinomimetic). Marketing of the acetylcholine esterase inhibitor, tacrine, has demonstrated that improvement in memory can be shown in patients with mild to moderate Alzheimer's Disease [M. Williams, Curr. Opin. Invest. Drugs, 2(5), 541–544 (May 1993)]. The utility of this drug is limited, however, because of adverse side effects especially at the higher doses where it is most effective. Clinical studies using the natural alkaloid, arecoline, a cholinergic agonist, have also demonstrated memory improvement in patients with mild to moderate Alzheimer's Disease. Because of the short half-life of arecoline, the clinical study was done using continuous infusion of the drug over a 2 week period. In addition, a peripheral muscarinic antagonist, N-methylscopolamine, was also administered during the study to prevent potential autonomic side effects. [T. T. Soncrant et al., Psychopharmacology, 112, 421–427 (1993)].

Cholinergic receptors which bind to and are activated by the alkaloid, muscarine, are called muscarinic receptors. Three pharmacologically defined subtypes of muscarinic receptors have been identified. They are referred to as M1, M2, and M3 based upon their affinity for the M1 antagonist, pirenzepine, the M2 antagonist, AFDX-116, and the M3 antagonist, 4-[(diphenylacetyl)oxy]-1,1-dimethylpiperidinium iodide (4-DAMP). Five different human muscarinic receptors have been cloned. The Hm1 (human m1) receptor is found primarily in the frontal cortex. [T. I. Bonner, Trends in Pharmacological Sciences, supplement, Jul. 20–27 (1989) p11–15, ]. Activation of the m1 receptor results in an increase in phosphoinsoitide hydrolysis (PI turnover).[K. Fukuda, et al., Ibid,. p. 4–10].

EP-307-142-A discloses a group of azacyclic thiadiazole derivatives as useful central acetylcholine agonists and analgesics.

DESCRIPTION OF THE INVENTION

In accordance with this invention there is provided a group of 2-aroylaminothiazole derivatives which bind to and stimulate central muscarinic acetylcholine receptors and are useful agents for treating symptoms of cognitive disorders, specifically the impaired memory associated with a decrease in the neurotransmitter, acetylcholine. Some of the compounds of this invention also bind to 5HT1A receptors and dopamine $D_2$ receptors, making them useful as antipsychotic agents.

The compounds of the present invention are characterized by the general formula:

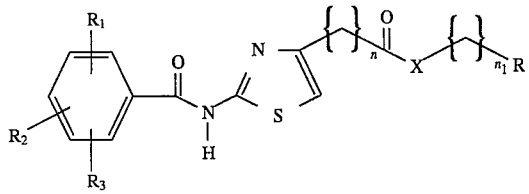

where $R_1$, $R_2$ and $R_3$ are, independently, H, alkyl of 1 to 6 carbon atoms, halo, perhaloalkyl of 1 to 6 carbon atoms, hydroxy, alkoxy of 1 to 6 carbon atoms, aryl of 6 to 10 carbon atoms or arylalkyl of 7 to 12 carbon atoms;

n is one of the integers 0, 1, 2, 3, 4 or 5;

R is azabicyclo[2.2.2]octyl or azabicyclo[2.2.1]heptyl when $n_1$ is zero, or R is $NR_4R_5$ when $n_1$ is 1, 2, 3, 4, or 5, in which $R_4$ and $R_5$ are alkyl of 1 to 6 carbon atoms or $R_4$ and $R_5$, taken with the nitrogen atom to which they are attached, are N-(substituted aryl)piperazinyl in which said substituent is alkoxy of 1 to 6 carbon atoms, halo, or perhaloalkyl of 1 to 6 carbon atoms, and the aryl group contains 6 to 10 carbon atoms; N-(pyridyl)piperazinyl; N-(pyrimidinyl)piperazinyl; or 3-azabicyclo-[3.2.2]non-3-yl;

X is oxygen or NH;

n and $n_1$ are, independently, one of the integers 0, 1, 2, 3, 4 or 5;

or a pharmaceutically acceptable salt thereof.

Of the compounds of the above-described genus, it is preferred that the variables representing $R_1$, $R_2$ and $R_3$ are 4-hydroxy and two alkyl groups, each containing 1 to 6 carbon atoms, more preferably the two alkyl groups are tertiary butyl, most preferably in the 3 and 5 positions and the preferred value of n is 0 and the preferred value of X is oxygen.

The pharmaceutically acceptable salts are those derived from such organic and inorganic acids as: acetic, lactic, citric, fumaric, tartaric, succinic, maleic, malonic, hydrochloric, hydrobromic, phosphoric, nitric, sulfuric, methanesulfonic, methylbenzene sulfonic, and similarly known acceptable acids.

The compounds of this invention bind to M1 receptors in rat brain and are capable of reversing hyperactivity produced in rodents by the M1 antagonist, scopolamine. They also reverse scopolamine-induced cognitive impairment in rodents in an 8-arm radial maze paradigm. Compounds with this activity are useful as antidementia agents. In addition some of the compounds of this invention bind to the serotonin receptor, $5HT_{1A}$ and the dopamine receptor, $D_2$. Compounds with this activity are useful as antipsychotic/anxiolytic/antidepressant agents.

The 3-azabicyclo[2.2.1] heptanes of this invention can exist as endo and exo isomers, racemates, and enantiomers. The azabicyclo[2.2.2] compounds can be racemates or enantiomers. These stereo and optical isomers may be isolated by conventional means.

The compounds of the present invention are prepared by the general synthetic methods detailed in Scheme I

SCHEME I

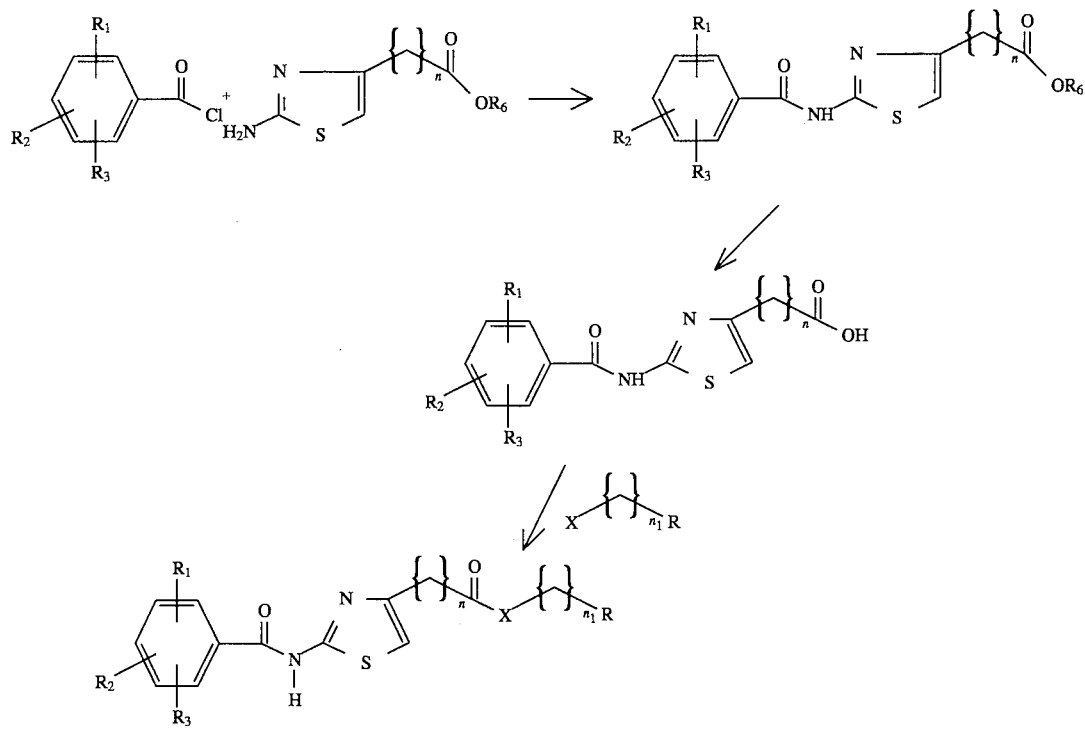

where R, $R^1$, $R^2$, $R^3$, n and $n_1$ are as described above; X is O, NH, or OH, $NH_2$; and $R_6$ is alkyl.

Referring to Scheme I, the requisite substituted or unsubstituted aroylchloride starting material is allowed to react with 2-aminothiazole-4-acetic or carboxylic acid ester in an organic solvent, such as tetrahydrofuran (THF) in the presence of a base, such as triethylamine (TEA) at temperatures of from 30° to 60° C. to give 2-aroylamidothiazole-4-acetic or carboxylic acid esters which are treated with a base, such as aqueous sodium hydroxide to give the corresponding carboxylic acids. The acids are allowed to react with an appropriate alcohol or amine in the presence of a coupling agent, such as bis(2-oxo-3-oxazolidinyl)phosphinic chloride (BOP-Cl) or dicyclohexylcarbonyldiimide (DCC) in an organic solvent, such as methylene chloride in the presence of a base, such as triethylamine to give products of this invention.

The following examples are presented for illustrative purposes only and are not to be construed as limitations for the disclosed invention. Those skilled in the art will be aware of other methods of preparing compounds of this invention. The starting materials or intermediates are available commercially or can be prepared by standard literature procedures.

EXAMPLE 1

2- [[3.5.-Bis( 1.1-dimethylethyl)-4-hydroxybenzoyl] amino]-4-thiazolecarboxylic acid 2-(dimethylamino)ethyl ester 2-Amino-4-thiazolecarboxylic acid ethyl ester (16.2 g, 100 mmol) and triethylamine (TEA, 10.5 g, 104 mmol) were combined in anhydrous tetrahydrofuran (THF, 200 mL) in a nitrogen atmosphere. To this was added slowly with stirring a solution of 3,5-bis(1,1-dimethylethyl)-4-hydroxybenzoyl-chloride (28 g, 104 mmol) in THF (100 mL). The reaction mixture was heated under reflux and monitored for disappearance of starting material by TLC (silica gel, 2% methanol in methylene chloride). After two days, the reaction mixture was cooled to room temperature and filtered to give 14.67 g of 2-[[[3,5-Bis(1,1-dimethylethyl)-4-hydroxyphenyl]-carbonyl]-amino]-4 -thiazolecarboxylic acid ethyl ester as a white solid, m.p. 233°–235° C. The filtrate was poured into ice water and extracted five times with diethyl ether. The ether phase was dried and evaporated and the residue was purified by flash chromatography on silica gel eluting with 20:80 hexane:methylene chloride to give 29.41 g of additional ethyl ester.

The ethyl ester (5 g, 12.4 mmol) was dissolved in THF (100 mL) and treated with 1N NaOH (37 mL, 37 mmoL, 3 equivalents) at room temperature with stirring overnight. TLC analysis of the orange reaction mixture (silica gel, 1:1 ethyl acetate:hexane) revealed no remaining ester starting material and a single baseline spot. The THF was removed on a rotary evaporator and the residue was dissolved in water (150 mL), acidified with 5 equivalents of 1N HCl (62 mL) and the gelatenous precipitate was collected by filtration and dried at 80° C. and 25 mm of Hg vacuum to give 2.67 g (57%) of 2-[[[3,5-Bis(1,1-dimethylethyl)-4-hydroxyphenyl] carbonyl]-amino]-4 -thiazole-carboxylic acid. Recrystallization from dioxane:heptane gave the acid as a white solid: m.p. 291°–293° C.

To a stirred suspension of the above thiazolecarboxylic acid (2.00 g, 5.3 mmol) in methylene chloride (25 mL), TEA (1.5 mL, 10.6 mmol) was added to give an orange solution. To the solution was added N,N-dimethylethanolamine (0.64 mL, 6.4 mmol) and bis(2-oxo-3-oxazolidinyl)phosphinic chloride (BOP-Cl, 1.35 g, 5.3 mmol). The reaction mixture was stirred under a nitrogen atmosphere for 4 hours. After quenching with saturated $NaHCO_3$ solution, methylene chloride (25 mL) was added and the phases were separated and the aqueous phase was washed with methylene chloride (25 mL). The combined organic phases were dried, filtered, and evaporated under reduced pressure to give an orange oily solid. Purification of the solid on silica gel eluting with 2–5% methanol in ethyl acetate gave the title compound as a yellow glass (0.84 g, 35%). Preparation of a monohydrochloride salt using ethereal HCl and diethyl ether gave a white solid. The solid was dissolved in ethyl acetate with mild warming, filtered and precipitated with hexane to give the pure product as off-white, monohydrochloride crystals: m.p. 138° C. foam).

Elemental analysis for: $C_{23}H_{33}N_3SO_4 \bullet HCl$

Calc'd: C, 57.07; H, 7.08; N, 8.68
Found: C, 56.90; H, 7.27; N, 8.31

EXAMPLE 2

2-[[3,5,-Bis(1.1-dimethylethyl)-4-hydroxybenzoyl]amino]-N-[2 -(dimethylamino)ethyl]-4-thiazolecarboxamide Following the procedure of Example 1 and substituting N,N-dimethylethylenediamine gave the title compound in 78% yield. The free base was converted to the dihydrochloride salt using ethereal HCl : m.p.181°–182° C.

Elemental analysis for: $C_{23}H_{34}N_4O_3S \bullet 2HCl \bullet 2.75 H_2O$

Calc'd: C, 48.54; H, 7.35; N, 9.85
Found: C, 48.35; H, 7.54; N,.9.70

EXAMPLE 3

N-[2-3-Azabicyclo[3.2.2]non-3-yl)ethyl-2-[[3.5-bis(1,1-dimethylethyl)-4 -hydroxybenzoyl]amino]-4-thiazolecarboxamide Bromoacetonitrile (12 g, 100 mmol), 3-azabicyclo[3.2.2.]nonane (12.6 g, 97 mmol) and triethylamine (TEA, 13.9 mL, 100 mmol) were combined in N,N-dimethylformamide (DMF, 400 mL) and heated at 50° C. for 72 hours. Evaporation of the DMF under high vacuum gave a residue which was partitioned between methylene chloride and water. Evaporation of the organic phase under reduced pressure and drying under vacuum gave N-cyanomethyl-3-azabicyclo[3.2.2.]nonane (I, 13 g, 81%). Reduction of (I, 10.42 g, 63.6 mmol) with lithium aluminum hydride (LiAlH₄, 3.62 g, 95.3 mmol) in dry THF under a nitrogen atmosphere at 0°–25° C. for 24 hours gave N-aminoethyl-3-azabicyclo [3.2.2.]nonane (II, 8.2 g, 76%) after purification by high pressure liquid chromatography on silica gel.

Following the procedure of Example 1 and substituting II gave the title compound in 26% yield. The free base was convened to the p-toluenesulfonic acid salt. Recrystallization from ethanol:ethyl acetate gave a white solid: m.p. 275°–276° C.

Elemental analysis for: $C_{29}H_{42}N_4O_3S \bullet C_7H8O_3S \bullet 0.33 H_2O$ Calc'd: C, 61.24; H, 7.24; N,7.95
Found: C, 61.33; H, 7.15; N,.8.06

EXAMPLE 4

2-[[3.5-Bis( 1.1-dimethylethyl)-4-hydroxybenzoyl]amino ]-4-thiazolecarboxylic acid 2-(3-azabicyclo[3.2.2.]non-3-yl)ethyl ester Following the procedure of Example 3 but substituting 2-bromoethanol for bromoacetonitrile and stopping after the first step gave N-2-hydroxethyl-3-azabicyclo[3.2.2.]nonane (III). Reaction of III with the thiazole-4-carboxylic acid of Example 1 according to the same procedure gave the title compound in 27% yield. The free base was converted to the p-toluenesulfonic acid salt to give an amorphous white solid.

Elemental analysis for: $C_{29}H_{41}N_3O_4S \bullet C_7H_8O_3S \bullet 0.75 H_2O$ Calc'd: C, 60.60; H, 7.13; N,5.89
Found: C, 60.63; H, 7.03; N,5.72

EXAMPLE 5

N-[3-(3-Azabicyclo[3.2.2]non-3-yl)propyl-2-[[3.5-bis(1.1-dimethylethyl)-4 -hydroxybenzoyl]amino]-4-thiazolecarboxamide Following the procedure of Example 3 but using 3-bromopropionitrile gave the title compound in 35% yield after passing the crude product through a pad of silica gel and eluting with ethyl acetate.

Reaction of the free base with p-toluenesulfonic acid gave the corresponding salt: m.p. 99°–101° C.

Elemental analysis for: $C_{30}H_{44}N_4O_3S \bullet C_7H8O_3S \bullet 1.25H_2O$ Calc'd: C, 60.42; H, 7.46; N, 7.61
Found: C, 60.32; H, 7.05; N, 7.14

EXAMPLE 6

N-[4-(3-Azabicyclo[3.2.2]non-3-yl)butyl]-2-[[3,5-bis(1,1-dimethylethyl)-4-hydroxybenzoyl]amino]-4-thiazolecarboxamide Following the procedure of Example 3 but using 4-bromobutyronitrile gave the title compound in 50% yield after passing the crude product through a pad of silica gel and eluting with 5% methanol in ethyl acetate. Reaction of the free base with ethereal HCl gave the dihydrochloride, hemihydrate: m.p. 180° C. (decomposed).

Elemental analysis for: $C_{31}H_{46}N_4O_3S \bullet 2 HCl \bullet 0.5 H_2O$

Calc'd: C, 58.48; H,7.76; N, 8.79
Found: C, 58.19; H, 7.67; N, 8.46

EXAMPLE 7

N-( 1-Azabicyclo[2.2.2]oct-3-yl)-2-[[3,5-bis(1,1-dimethylethyl-4 -hydroxybenzoyl]amino]-4-thiazolecarboxamide Following the procedure of Example 1 but using 3-amino-1-azabicyclo[2.2.2]octane gave the title compound in 8% yield after workup. The crude product was partitioned between 9:1 ethyl acetate: methanol and saturated NaCl solution. The aqueous phase was extracted with ethyl acetate. The organic phases were combined, washed with saturated NaCl, dried and evaporated to give the title compound. Reaction of the free base with ethereal HCl gave the dihydrochloride, monohydrate: m.p. 180° C. (decomposed).

Elemental analysis for: $C_{26}H_{36}N_4O_3S \bullet 2 HCl \bullet 1.0 H_2O$

Calc'd: C, 54.25; H, 7.01; N,9.73
Found: C, 54.39; H, 6.95; N,.9.53

EXAMPLE 8

N-(1-Azabicyclo[2.2.2]oct-3-yl-2-[(4-(phenylmethoxy)benzoyl]amino]-4 -thiazolecarboxamide 2-Amino-4-thiazolecarboxylic acid ethyl ester (6.85 g, 39.8 mmol) was allowed to react with 4-phenylmethoxybenzoyl chloride (10.72 g, 43.8 mmol) according to the procedure in Example 1. The reaction was completed in 18 hours. After workup and flash chromatography on silica gel eluting with 1–7% acetonitrile in methylene chloride, the ethyl ester of 2-[[ 4-phenylmethoxybenzoyl]amino]-4-thiazolecarboxylic acid was obtained (70% yield) and was hydrolyzed to the corresponding acid with 1.0N NaOH as described in Example 1.

Following the procedure of Example 1 but using 3-amino-1-azabicyclo[2.2.2]octane gave the title compound in 12% yield. The free base was converted to the dihydrochloride salt with ethereal HCl to give the 1.5 hydrate as a white solid: m.p. 196° C. (decompose).

Elemental analysis for: $C_{25}H_{26}N_4O_3S \bullet 2\ HCl \bullet 1.5\ H_2O$
Calc'd: C, 53.38; H, 5.56; N, 9.96
Found: C, 53.45; H, 5.48; N,.9.86

EXAMPLE 9

N-[4-(3-Azabicyclo[3.2.2non-3-yl)butyl]-2-[[4-phenylmethoxy)benzoyl]amino] -4-thiazolecarboxamide 2-[[4-phenymethoxybenzoyl]amino]-4-thiazolecarboxylic acid (1.28 g, 3.62 mmol) was allowed to react with N-(4-aminobutyl)-3-azabicyclo[3.2.2.]nonane(0.751 g, 3.65 mmol) following the procedure of Example 1 to give the title compound after flash column chromatography on silica gel eluting with 5% methanol in ethyl acetate. The free base was converted to the dihydrochloride salt using ethereal HCl to give the salt as a white solid: m.p. 145°–147° C.

Elemental analysis for: $C_{30}H_{36}N_4O_3S \bullet 2\ HCl$
Calc'd: C, 59.50; H, 6.32; N, 9.25
Found: C, 59.12; H, 6.35; N, 8.98

EXAMPLE 10

N-[3-( 3- Azabicyclo[3.2.2]non-3-yl)propyl-2-[[4-hydroxybenzoyl]amino-4 -thiazolecarboxamide N-[3-(3-Azabicyclo[3.2.2]non-3-yl)propyl-2-[[4-phenylmethoxy)benzoyl]amino]-4 -thiazolecarboxamide (764 mg, 1.47 mmol) was stirred in a nitrogen atmosphere at room temperature with 500 mg of 10% Pd on carbon in ethanol containing 1 equivalent of sodium formate and 4 equivalents of formic acid. After three days, the reaction mixture was filtered through Solkafloc® and the filtrate was evaporated under vacuum. The residue was purified by chromatography on silica gel eluting with 3:7 methanol:ethyl acetate to give the title compound. The dihydrochloride salt was formed using ethereal HCl: m.p.168° C. (decomposed).

Elemental analysis for: $C_{22}H_{28}N_4O_3S \bullet 2\ HCl$
Calc'd: C, 52.69; H, 6.03; N, 11.07
Found: C, 53.01; H,6.22; N, 10.87

EXAMPLE 11

N-[4-(3-Azabicyclo[3.2.2]non-3-yl)butyl-2-[[4-hydroxybenzoyl]amino]-4 -thiazolecarboxamide Following the procedure of Example 10, N-[2-(4-azabicyclo[3.2.2]non-3 -yl)butyl-4-[[3-phenylmethoxy)benzoyl]amino]-4-thiazolecarboxamide was converted to the title compound, which was purified by chromatography on silica gel eluting with 5:95 methanol:ethyl acetate containing traces of ammonium hydroxide (about 0.5 mL for every 100 mL of eluant). The dihydrochloride of the title compound was prepared using ethereal HCl to give a white solid: 265° C. (decompose).

Elemental analysis for: $C_{23}H_{30}N_4O_3S \bullet 2\ HCl$
Calc'd: C, 53.59; H, 6.52; N, 10.86
Found: C, 53.27; H, 6.32; N, 10.44

EXAMPLE 12

N-[4-(3-Azabicyclo[3.2.2]non-3-yl)butyl-2-[(4-fluorobenzoyl)amino]-4 -thiazoleacetamide 2-Amino-4-thiazoleacetic acid ethyl ester (1.86 g, 10 mmol mmol) was allowed to react with 4-fluorobenzoyl chloride (1.74 g, 11 mmol) in dry THF (10 mL) containing dry pryidine (0.9 mL, 11 mmol) for 48 hours at room temperature (23° C.) under a nitrogen atmosphere. The thick precipitate which formed was isolated by filtration, dissolved in diethyl ether:THF, washed with water, saturated NaCl,and then with saturated NaHCO₃. The organic phase was separated, dried over MgSO₄ and evaporated. The residue was suspended in diethyl ether and filtered to give the acylated ester (1.42 g) as an off-white solid. Evaporation of the tiltrate gave a golden solid (1.27 g) which was mostly the desired product by TLC (silica gel, 1:9 methanol:methylene chloride). The two fractions were combined and recrystallized from diethyl ether (90 mL) to give 1.78 g (58%) of the 2-[[4-fluorobenzoyl]amino]-4 thiazoleacetic acid ethyl ester: m.p. 110°–112° C. Hydrolysis to 2-[[4-fluorobenzoyl]amino]-4 -thiazoleacetic acid was accomplished using 1N NaOH as described in Example 1.

Following the procedure of Example 1, 2-[[4-fluorobenzoyl]amino]-4-thiazoleacetic acid (1.10 g, 3.93 mmol) was allowed to react with N-(4-aminobutyl)-3-azabicyclo[3.2.2.] -nonane (0.77 g, 3.13 mmol) for 24 hours to give after flash column chromatography on silica gel eluting with 15% methanol in ethyl acetate, the title compound (0.79 g, 57%). The hydrochloride salt was prepared with ethereal HCl to give a tan powder after recrystallization from ethyl acetate and hexane: m.p. 220°–222° C.

Elemental analysis for: $C_{24}H_{31}FN_4O_{22}S \bullet HCl \bullet 0.25\ H_2O$
Calc'd: C, 57.70; H, 6.56; N, 11.22
Found: C, 57.78; H, 6.51; N, 10.95

EXAMPLE 13

2-[(4-Fluorobenzoyl)amino]-4-thiazoleacetic acid 3-[4-(2-methoxyphenyl)-1 -piperazinyl]propyl ester (4-Fluorobenzoyl)amino]-4-thiazoleacetic acid (2.8 g, 10 mmol) and N-(3-hydroxypropyl) -N'-(2'-methoxyphenyl)piperazine (2.5 g, 10 mmol) were allowed to react in the presence of DCC (2.5 g, 12 mmol) and N,N-dimethylaminopyridine (DMAP, 122 mg, 1 mmol)) in methylene chloride (160 mL) to give the title compound as a white solid: m.p. 100° C.

Elemental analysis for: $C_{26}H_{29}N_6FN_4O_4S \bullet \frac{1}{6}\ CH_2Cl_2$ (confirmed by NMR)
Calc'd: C, 59.08; H, 5.49; N, 10.61
Found: C, 59.21; H, 5.60; N, 10.57

EXAMPLE 14

2-[[[3,5-Bis(1,1-dimethylethyl)-4-hydroxyphenyl]carbonyl]amino]-4 -thiazoleacetic acid 3-[4-(2-methoxyphenyl)-1-piperazinyl]propyl ester Following the procedure of Example 13, 3,5-Bis(1,1-dimethylethyl)-4hydroxyphenyl]carbonyl]amino]-4 -thazoleacetic acid and N-(3-hydroxypropyl)-N'(2'-methoxyphenyl)piperazine were allowed to react in the presence of DCC and N,N-dimethylaminopyridine (DMAP) in methylene chloride to give the title compound as a yellow foam.

Elemental analysis for: $C_{34}H_{46}N_4O_5S$
Calc'd: C, 65.57; H, 7.44; N, 9.00
Found: C, 65.04; H, 7.57; N, 8.06

EXAMPLE 15

2-[[[3,5-Bis( 1.1-dimethylethyl)-4-hydroxyphenyl]carbonyl]-4 thiazoleacetic acid 2-[4-(2-methoxyphenyl)-1-piperazinyl]propyl ester Following the procedure of Example 13, 3,5-Bis( 1,1 -dimethylethyl)-4-hydroxyphenyl] carbonyl]amino]-4-thiazoleacetic acid (3.00 g, 7.7 mmol) and N-(2 -hydroxyethyl)-N'-(2'-methoxyphenyl)piperazine (1.81 g, 7.7 mmol) were allowed to react in the presence of DCC (1.75 g, 8.47 mmol)

and N,N-dimethylaminopyridine (DMAP, 93 mg, 0.77 mmol) in methylene chloride (90 mL) to give the title compound as an orange oil. Treatment with ethereal HCl gave 2.90 g of a tan solid which was recrystallized from acetonitrile and toluene to give 1.73 g of the dihydrochloride salt as a white solid: m.p. 201°–205° C.

Elemental analysis for: $C_{33}H_{46}N_4O_5S\bullet 2HCl$
Calc'd: C, 57.97; H, 7.08; N, 8.19
Found: C, 58.30; H, 6.83; N, 7.83

EXAMPLE 16

2-[ (4-Fluorobenzoyl)amino]-4-thiazoleacetic acid 2-[4-(2-pyrimidinyl)-1-piperazinyl]ethyl ester Following the procedure of Example 13, (4-fluorobenzoyl)amino]-4-thiazoleacetic acid (4.2 g, 15 mmol) and N-(2-hydroxyethyl)-N'-(2-pyrimidinyl)piperazine (3.12 g, 15 mmol) were allowed to react in the presence of DCC (3.75 g, 18 mmol) and N,N-dimethylaminopyridine (DMAP, 183 mg, 1.5 mmol) in methylene chloride (240 mL) to give the title compound 5.46 g (77%) after purification by flash chromatography on silica gel eluting with 1:1 THF: hexane. The free base was converted to the dihydrochloride salt by treatment with ethereal HCl to give an off-white solid: m.p. 205°–207° C.

Elemental analysis for: $C_{22}H_{24}N_6OF_3S\bullet 2HCl$
Calc'd: C, 48.62; H, 4.64; N, 15.14
Found: C, 48.30; H, 4.55; N, 15.28

EXAMPLE 17

2-[[3,5 Bis(1,1-dimethylethyl-4-hydroxybenzoyl]amino]-N-[2-[-4-(2 -pyrimidinyl)-1-peperazinyl]ethyl]-4-thiazoleacetamide 3,5 Bis(1,1-dimethylethyl)-4-hydroxybenzoyl]amino-4-thiazoleacetic acid (3 g, 7.7 mmol) was converted to the corresponding acid chloride with thionyl chloride in petroleum ether and then allowed to react with N-(2-aminoethyl)-N'-(2pyrimidinyl)piperazine (1.75 g, 8.47 mmol) in THF containing TEA (2.15 mL, 15.4 mmol) at room temperature overnight. Evaporation of the volatiles under vacuum gave a residue which was purified by HPLC to give the title compound as a brown oil which crystallized upon trituration with hexane. Recrystallization from benzene and hexane gave 223 mg of the title compound as a tan solid: m.p. 175°–179° C.

Elemental analysis for: $C_{30}H_{41}N_7O_3S$
Calc'd: C, 62.15; H, 7.13; N, 16.91
Found: C, 61.84; H, 7.00; N, 16.99

The selective $M_1$ muscarinic binding by the compounds of this invention was established by determining the $IC_{50}$ concentration of the test compound that will cause a fifty percent inhibition of specific [$^3$H]pirenzepine binding to rat brain tissue ($IC_{50}$). Similarly, the $IC_{50}$ value for a representative compound was determined by $M_2$ receptor binding at cerebellum tissue which contains a high portion of $M_2$ receptors, relative to [$^3$H]quinuclidinyl benzilate (QNB). Comparison of the results obtained in these in vitro studies indicates the relative selectivity of the test compound for binding at the post-synaptic cholinergic $M_1$ and $M_2$ receptors which are mainly found in the central nervous system.

Certain compounds of this invention also possess high affinity for the dopamine D-2 receptor and the serotonin 5-HT$_{1A}$ receptor, and consequently, they are additionally useful as antipsychotic, antidepressant and anxiolytic agents for the treatment of a variety of central nervous system disorders such as depression, paranoia, schizophrenia, anxiety, sleep disorders, sexual dysfunction, addiction, and related problems.

High affinity for the dopamine D-2 receptor was established by the standard experimental test procedure of Fields, et al., Brain Res., 136, 578 (1977) and Yamamura et al., eds., Neurotransmitter Receptor Binding, Raven Press, N.Y. (1978) wherein homogenized limbic brain tissue is incubated with $^3$H-spiroperidol and various concentrations of test compound, filtered and washed and shaken with Hydrofluor scintillation cocktail (National Diagnostics) and counted in a Packard 460 CD scintillation counter. The results of this testing with the relevant compounds of this invention are given below.

High affinity for the serotonin 5-HT$_{1A}$ receptor was established by testing the claimed compound's ability to displace [$^3$H]8-OHDPAT (dipropylaminotetralin) from the 5-HT$_{1A}$ serotonin receptor following the procedure of Hall et al., J. Neurochem. 44, 1685 (1985). This procedure is employed to analogize this property of the claimed compounds with that of buspirone, which is a standard for anxiolytic activity, and, like the compounds of this invention, displays potent affinity for the 5-HT$_{1A}$ serotonin receptor subtype. The anxiolytic activity of buspirone is believed to be, at least partially, due to its 5-HT$_{1A}$ receptor affinity (Vander Maclen et al., Eur. J. Pharmacol. 1986, 129 (1–2) 133–130).

The results of these studies are given below:

| Example | $M_1$ [$^3$H] PZ binding in rat cortex at 1 μM % inhibition | $M_2$ [$^3$H] QNB binding in rat cerebellum % inhibition | D-2 Binding (% Inhibition at 1 μM) | 5-HT$_{1A}$ Binding (% Inhibition at 1 μM) |
|---|---|---|---|---|
| 1 | $IC_{50}$ = 0.054 μM | $IC_{50}$ = 3.4 μM | | |
| 2 | 98.6 | | | |
| 3 | 70.5 | | | |
| 4 | 90.6 | | | |
| 5 | 78 | | | |
| 6 | 86 | | | |
| 7 | 104.5 | | | |
| 8 | 85.8 | | | |
| 9 | 62 | | | |
| 10 | 58.7 | | | |
| 11 | 63.9 | | | |
| 12 | 56.96 | | | |
| 13 | | | 81 | 100 |
| 14 | | | 91 | 89 |
| 15 | | | 51 | |
| 16 | | | 34 | |
| 17 | | | 5% at 0.1 μM | |

The compound of Example 1 was also tested in accordance with the procedure of Symons et al, Soc. Neuroscience Abstracts 12:2, 897 (1986) in which Male CFW mice, 25 to 35 grams in weight are given the test compound in suitable vehicle plus 0.3 mg/kg scopoolamine.HBr in suitable vehicle, i.p.(3 groups of 12 animals each) or vehicle alone (1 group of 12 animals ) or vehicle plus scopolamine. HBr (1 group of 12 animals). The rates are placed in a swim tank, individually, containing 10 cm H$_2$O for a period of 5 minutes and the distance each animal swims is recorded. The mean swimming distance for the group is compared with controls and the test compound is considered active at a dose that significantly reduces the distance swam from the scopolamine control mean swim distance. Similarly the test compound is considered active if its results do not differ from the vehicle control mean. The compound of Example 1, representative of the other compounds of this invention, exhibited activity by reversing the hyperactivity of scopolamine treated animals in this standard experimental test procedure at a mimimum effective dose of MED=3 mg/kg.

The compound of Example 1 was also tested in the eight arm radial maze test procedure in which Sprague-Dawley male rats at 85% of their free feeding weight are trained to obtain two food pellets from food cups placed at the ends of four of the eight arms radiating from a circular central area of the maze, in a five minute period. After training to a level of error (return to a previously entered arm is error) equal to or less than 2, the rats performance is disrupted with scopolamine HBr (0.3 mg/kg, s.c.) and test compound dosage (i.p.). The number of errors are then determined and compared with control receiving scopolamine alone. The compound of Example 1 exhibited a reversal of scopolamine disrupted rat performance at a minimum effective dose of MED=3 mg/kg.

Hence, the compounds of this invention demonstrated high affinity for muscarinic receptors (especially the m1 receptor) and are therefore useful in the treatment of disease states associated with insufficient cerebral acetylcholine production or release.

Based upon this receptor binding information, the compounds of this invention are characterized as useful in the treatment of cognitive disorders associated with decreased levels of cerebral acetylcholine production or release, such as presenile dementia, senile dementia of the Alzheimer's type, Parkinson's disease, Downe's Syndrome and dementia pugilitica.

As such, the compounds may be administered neat or with a pharmaceutical carder to a patient in need thereof. The pharmaceutical carrier may be solid or liquid.

Applicable solid carriers can include one or more substances which may also act as flavoring agents, lubricants, solubilizers, suspending agents, fillers, gildants, compression aids, binders or tablet-disintergrating agents or an encapsulating material. In powders, the carder is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carders include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific patient suffering from cerebral acetylcholine insufficiency must be subjectively determined by the attending physician. The variables involved include the severity of the dysfunction, and the size, age and response pattern of the patient.

What is claimed is:

1. A compound of the formula:

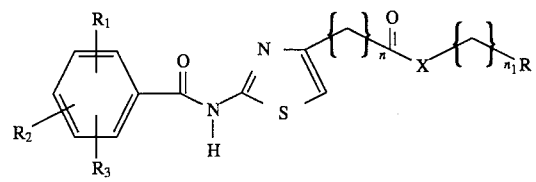

where $R_1$, $R_2$ and $R_3$ are, independently, H, alkyl of 1 to 6 carbon atoms, halo, perhaloalkyl of 1 to 6 carbon atoms, hydroxy, alkoxy of 1 to 6 carbon atoms, aryl of 6 to 10 carbon atoms or arylalkyl of 7 to 12 carbon atoms;

n is one of the integers 0, 1, 2, 3, 4 or 5;

R is azabicyclo[2.2.2] octyl or azabicyclo[2.2.1] heptyl when $n_1$ is zero, or R is $NR_4R_5$ when $n_1$ is 1, 2, 3, 4, or 5, in which $R_4$ and $R_5$ are alkyl of 1 to 6 carbon atoms or $R_4$ and $R_5$, taken with the nitrogen atom to which they are attached, are N-(substituted aryl)piperazinyl in which said substituent is alkoxy of 1 to 6 carbon atoms, halo, or perhaloalkyl of 1 to 6 carbon atoms, and the aryl group contains 6 to 10 carbon atoms; N-(pyridyl)piperazinyl; N-(pyrimidinyl)piperazinyl; or 3-azabicyclo-[3.2.2]non-3-yl;

X is oxygen or NH;

n and $n_1$ are, independently, one of the integers 0, 1, 2, 3, 4 or 5;

or a pharmaceutically acceptable salt thereof.

2. A compound of claim 1 in which $R_1$ and $R_3$ are alkyl of 1 to 6 carbon atoms and $R_2$ is 4-hydroxy.

3. A compound of claim 2 in which $R_1$ and $R_3$ are tertitary butyl substituents in the 3 and 5 positions.

4. A compound of claim 2 in which n is 0 and X is oxygen.

5. The compound of claim 1 which is 2-[[3,5,-bis(1,1-dimethylethyl)-4-hydroxybenzoyl]amino]-4-thiazolecarboxylic acid 2-(dimethylamino)ethyl ester, or a pharmaceutically acceptable salt thereof.

6. The compound of claim 1 which is 2-[[3,5,-bis(1,1-dimethylethyl)-4-hydroxybenzoyl]amino]-N-[2-(dimethylamino)ethyl]-4-thiazolecarboxamide, or a pharmaceutically acceptable salt thereof.

7. The compound of claim 1 which is N-[2-(3-azabicyclo [3.2.2]non-3-yl)ethyl-2-[[3,5-bis(1,1-dimethylethyl)-4-hydroxybenzoyl]amino]-4-thiazolecarboxamide, or a pharmaceutically acceptable salt thereof.

8. The compound of claim 1 which is 2-[[3,5-bis(1,1-dimethylethyl)-4hydroxybenzoyl] amino]-4-thiazolecarboxylic acid 2-(3-azabicyclo[3.2.2]non-3yl)ethyl ester, or a pharmaceutically acceptable salt thereof.

9. The compound of claim 1 which is N-[2-(3-azabicyclo [3.2.2]non-3-yl)propyl 3-[[3,5-bis(1,1 -dimethylethyl)-4-hydroxybenzoyl]amino]-4-thiazolecarboxamide, or a pharmaceutically acceptable salt thereof.

10. The compound of claim 1 which is N-[4-(3-azabicyclo [3.2.2]non-3-yl)butyl] -2-[[3,5-bis( 1,1-dimethylethyl)-4-hydroxybenzoyl]amino]-4-thiazolecarboxamide, or a pharmaceutically acceptable salt thereof.

11. The compound of claim 1 which is N-(1-azabicyclo [2.2.2]oct-3-yl)-2-[[3,5-bis (1,1-dimethylethyl-4-hydroxybenzoyl]amino]-4-thiazolecarboxamide, or a pharmaceutically acceptable salt thereof.

12. The compound of claim 1 which is N-(1-azabicyclo [2.2.2]oct-3-yl)-2-[(4(phenylmethoxy)benzoyl] amino]-4-thiazolecarboxamide, or a pharmaceutically acceptable salt thereof.

13. The compound of claim 1 which is N-[4-(3-azabicyclo [3.2.2]non-3-yl)butyl]    -2-[[4-phenylmethoxy)benzoyl] amino]-4-thiazolecarboxamide, or a pharmaceutically acceptable salt thereof.

14. The compound of claim 1 which is N-[4-(3-azabicyclo [3.2.2]non-3-yl)propyl -2-[[4-hydroxybenzoyl]amino]-4-thiazolecarboxamide, or a pharmaceutically acceptable salt thereof.

15. The compound of claim 1 which is N-[4-(3-azabicyclo [3.2.2]non-3-yl)butyl -2-[[4-hydroxybenzoyl]amino]-4-thiazolecarboxamide, or a pharmaceutically acceptable salt thereof.

16. The compound of claim 1 which is N-[4-(3-azabicyclo [3.2.2]non-3-yl)butyl -2-[(4-fluorobenzoyl)amino]-4-thiazoleacetamide or a pharmaceutically acceptable salt thereof.

17. The compound of claim 1 which is 2-[(4-fluorobenzoyl)amino]-4-thiazoleacetic acid 3-[4-(2-methoxyphenyl)-1-piperazinyl]propyl ester, or a pharmaceutically acceptable salt thereof.

18. The compound of claim 1 which is 2-[[[3,5-bis(1,1-dimethylethyl)-4hydroxyphenyl] carbonyl]amino]-4-thiazoleacetic acid 3-[4-(2-methoxyphenyl)- 1piperazinyl] propyl ester, or a pharmaceutically acceptable salt thereof.

19. The compound of claim 1 which is 2-[[[3,5-bis(1,1-dimethylethyl)-4-hydroxyphenyl] carbonyl]amino]-4-thiazoleacetic acid 2-[4-(2-methoxyphenyl)-piperazinyl]ethyl ester, or a pharmaceutically acceptable salt thereof.

20. The compound of claim 1 which is 2-[(4-fluorobenzoyl)amino]-4-thiazoleacetic acid 2-[4-(2-pyrimidinyl)-1-piperazinyl]ethyl ester, or a pharmaceutically acceptable salt thereof.

21. The compound of claim 1 which is 2-[[3,5-bis(1,1-dimethylethyl)-4-hydroxybenzoyl] amino]-N-[2-{4-(2-pyrimidinyl)- 1-piperazinyl]ethyl]-4-thiazoleacetamide, or a pharmaceutically acceptable salt thereof.

* * * * *